United States Patent
Kieval

(10) Patent No.: US 6,616,624 B1
(45) Date of Patent: Sep. 9, 2003

(54) SYSTEMS AND METHOD FOR CONTROLLING RENOVASCULAR PERFUSION

(75) Inventor: Robert S. Kieval, Medina, MN (US)

(73) Assignee: CVRX, Inc., Maple Grove, MN (US)

(*) Notice: Subject to any disclaimer, the term of this patent is extended or adjusted under 35 U.S.C. 154(b) by 0 days.

(21) Appl. No.: 09/702,089

(22) Filed: Oct. 30, 2000

(51) Int. Cl.[7] .............................. A61M 5/00; A61B 5/02
(52) U.S. Cl. ........................ 604/8; 600/486; 600/505
(58) Field of Search .......................... 604/8; 600/485, 600/486, 505, 201, 202, 203, 204

(56) References Cited

U.S. PATENT DOCUMENTS

| | | | |
|---|---|---|---|
| 3,768,102 A | 10/1973 | Kwan-Gett et al. ................ 3/1 |
| 4,014,318 A | 3/1977 | Dockum et al. ............. 128/1 D |
| 4,053,952 A | 10/1977 | Goldstein ........................ 3/1.1 |
| 4,130,119 A | 12/1978 | Sessions et al. ............ 128/325 |
| 4,192,302 A * | 3/1980 | Boddie ....................... 604/5.04 |
| 4,256,094 A | 3/1981 | Kapp et al. ................ 128/24 R |
| 4,417,360 A | 11/1983 | Moasser ......................... 3/1.5 |
| 4,551,862 A | 11/1985 | Haber .......................... 623/14 |
| 4,586,501 A | 5/1986 | Claracq ....................... 128/325 |
| 4,682,583 A | 7/1987 | Burton et al. ............... 128/1 R |
| 4,709,690 A | 12/1987 | Haber .......................... 128/1 R |
| 4,781,672 A | 11/1988 | Hooven .......................... 604/9 |
| 4,828,544 A | 5/1989 | Lane et al. ...................... 604/9 |
| 4,877,035 A | 10/1989 | Bogen et al. ................ 128/673 |
| 4,881,939 A | 11/1989 | Newman ...................... 600/31 |
| 4,887,608 A | 12/1989 | Mohl et al. ................. 128/673 |
| 4,902,272 A | 2/1990 | Milder et al. ................. 600/18 |
| 4,969,470 A | 11/1990 | Mohl et al. ................. 128/673 |
| 5,019,055 A | 5/1991 | O'Boyle ....................... 604/249 |
| 5,509,888 A | 4/1996 | Miller ........................... 600/29 |
| 5,634,878 A | 6/1997 | Grundei et al. ................ 600/30 |
| 5,692,882 A | 12/1997 | Bozeman, Jr. et al. ......... 417/45 |
| 5,785,659 A | 7/1998 | Caro et al. ................... 600/485 |
| 5,813,410 A | 9/1998 | Levin .......................... 128/897 |
| 5,833,618 A * | 11/1998 | Caro et al. ................... 600/485 |
| 5,843,996 A | 12/1998 | Weglicki ..................... 514/557 |
| 5,891,012 A | 4/1999 | Downey et al. ............... 600/17 |
| 5,954,766 A | 9/1999 | Zadno-Azizi et al. ........... 623/2 |
| 6,086,527 A * | 7/2000 | Talpade ........................ 600/18 |
| 6,159,201 A * | 12/2000 | Hamilton et al. ............... 606/1 |
| 6,209,545 B1 * | 4/2001 | Zhukova et al. ............. 128/898 |
| 6,280,377 B1 | 8/2001 | Talpade ........................ 600/16 |
| 6,461,305 B1 * | 10/2002 | Schnall ........................ 600/485 |

FOREIGN PATENT DOCUMENTS

| | | |
|---|---|---|
| WO | WO 00/41612 | 7/2000 |
| WO | WO 00/51675 | 9/2000 |

\* cited by examiner

*Primary Examiner*—Alfred Basichas
(74) *Attorney, Agent, or Firm*—Townsend and Townsend and Crew LLP

(57) ABSTRACT

Devices, systems and methods by which the real or apparent renovascular perfusion and intrarenal pressure may be selectively and controllably increased. By selectively and controllably increasing renovascular perfusion and interstitial hydrostatic pressure when the heart is unable to pump sufficient blood or when renal perfusion is suboptimal, the present invention reduces or reverses neurohormonal activation and fluid retention, and thereby minimizes their deleterious effects on the heart, vasculature, kidneys and other body systems.

30 Claims, 11 Drawing Sheets

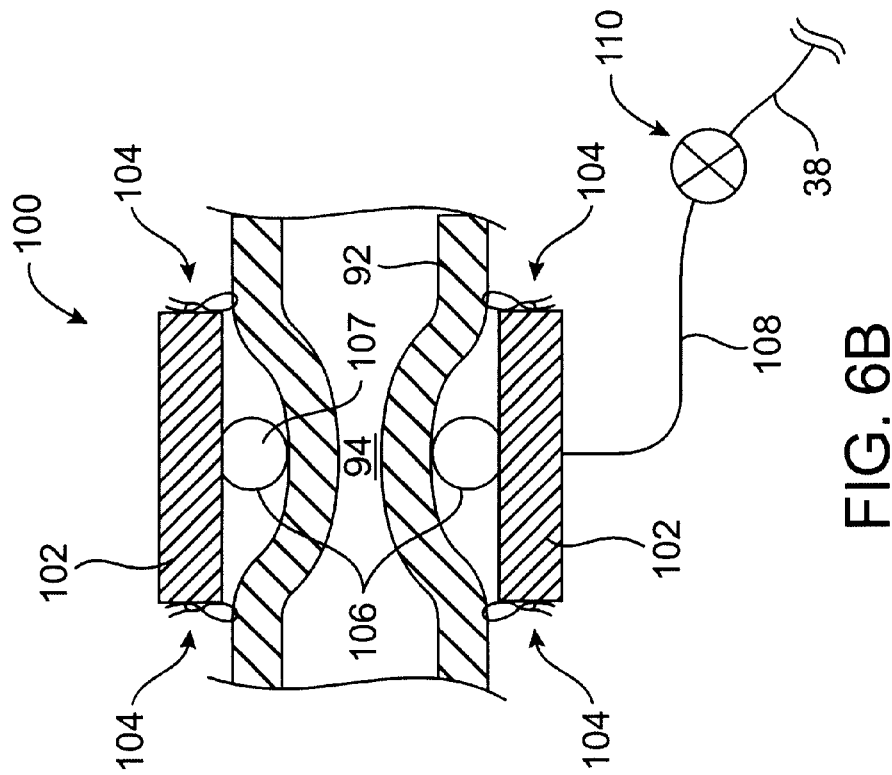
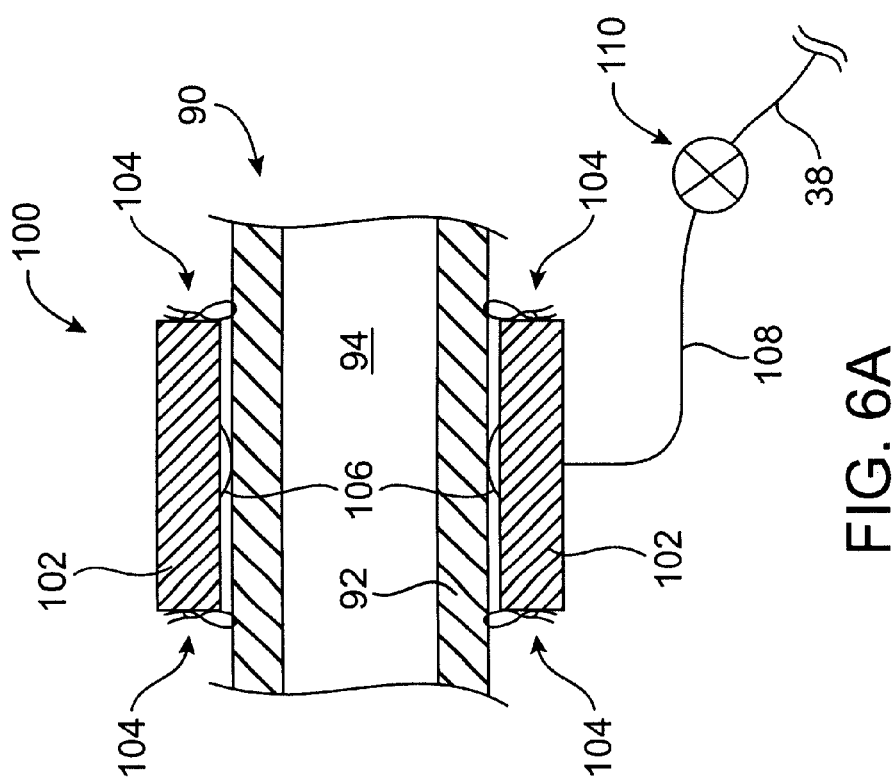

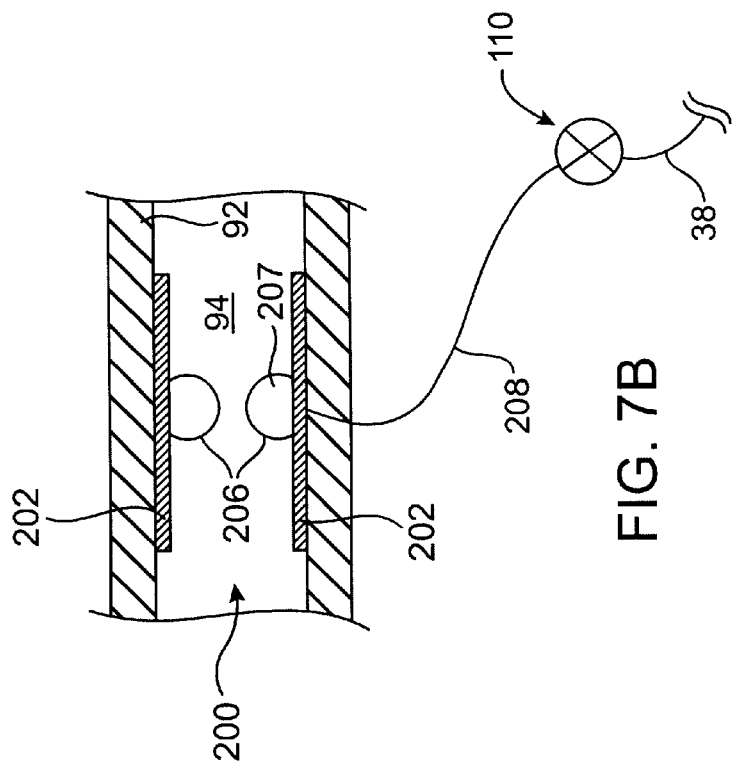
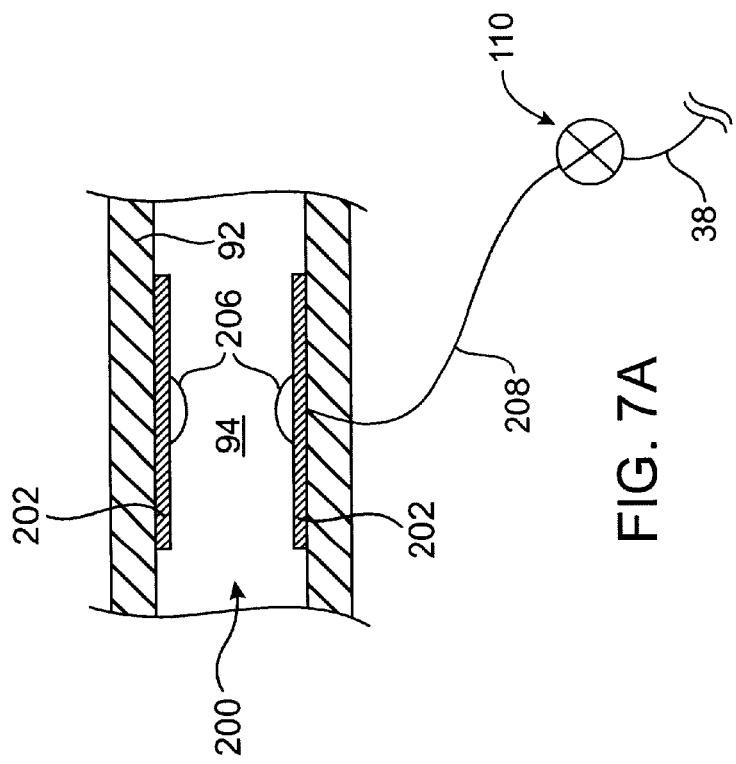

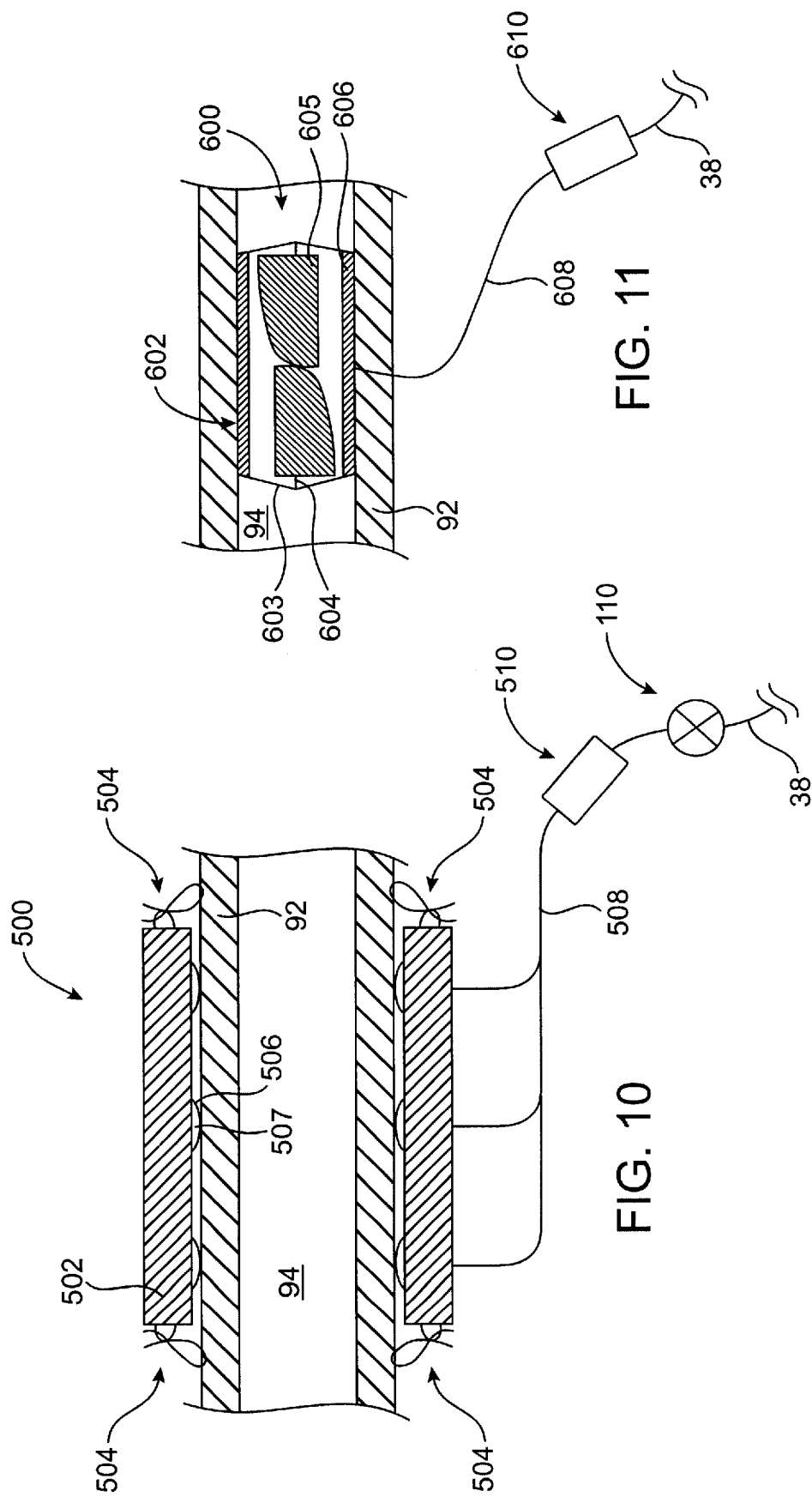

SYSTEMS AND METHOD FOR CONTROLLING RENOVASCULAR PERFUSION

FIELD OF THE INVENTION

The present invention generally relates to medical devices and methods of use for the treatment and/or management of cardiovascular and renal disorders. Specifically, the present invention relates to devices and methods for controlling renal perfusion in the renovascular system for the treatment and/or management of cardiovascular disorders such as hypertension and congestive heart failure, and renal disorders such as renal insufficiency and end stage renal disease.

BACKGROUND OF THE INVENTION

Cardiovascular disease is a major contributor to patient illness and mortality. It also is a primary driver of health care expenditure, costing more than $326 billion each year in the United States. Hypertension, or high blood pressure, is a major cardiovascular disorder that is estimated to affect over 50 million people in the United Sates alone. Of those with hypertension, it is reported that fewer than 30% have their blood pressure under control. Hypertension is a leading cause of heart failure and stroke. It is the primary cause of death in over 42,000 patients per year and is listed as a primary or contributing cause of death in over 200,000 patients per year in the U.S. Accordingly, hypertension is a serious health problem demanding significant research and development for the treatment thereof.

Hypertension occurs when the body's smaller blood vessels (arterioles) constrict, causing an increase in blood pressure. Because the blood vessels constrict, the heart must work harder to maintain blood flow at the higher pressures. Although the body may tolerate short periods of increased blood pressure, sustained hypertension may eventually result in damage to multiple body organs, including the kidneys, brain, eyes and other tissues, causing a variety of maladies associated therewith. The elevated blood pressure may also damage the lining of the blood vessels, accelerating the process of atherosclerosis and increasing the likelihood that a blood clot may develop. This could lead to a heart attack and/or stroke. Sustained high blood pressure may eventually result in an enlarged and damaged heart (hypertrophy), which may lead to heart failure.

Heart failure is the final common expression of a variety of cardiovascular disorders, including ischemic heart disease. It is characterized by an inability of the heart to pump enough blood to meet the body's needs and results in fatigue, reduced exercise capacity and poor survival. It is estimated that approximately 5,000,000 people in the United States suffer from heart failure, directly leading to 39,000 deaths per year and contributing to another 225,000 deaths per year. It is also estimated that greater than 400,000 new cases of heart failure are diagnosed each year. Heart failure accounts for over 900,000 hospital admissions annually, and it is the most common discharge diagnosis in patients over the age of 65 years. It has been reported that the cost of treating heart failure in the United States exceeds $20 billion annually. Accordingly, heart failure is also a serious health problem demanding significant research and development for the treatment and/or management thereof.

End stage renal disease (ESRD) affects over 300,000 people in the United States, with an annual incidence of over 79,000. Death from ESRD occurred in over 60,000 cases in 1998; the five year survival rate is less than 30%. Medicare payments in 1998 for the treatment of ESRD exceeded $10 billion. Accordingly, ESRD is a major health problem demanding improved therapy and management.

Heart failure results in the activation of a number of body systems to compensate for the heart's inability to pump sufficient blood. Many of these responses are mediated by an increase in the level of activation of the sympathetic nervous system as well as activation of multiple other neurohormonal responses. Generally speaking, this sympathetic nervous system activation signals the heart to increase heart rate and force of contraction to increase the cardiac output; it signals the kidneys to expand the blood volume by retaining sodium and water; and it signals the arterioles to constrict to elevate the blood pressure. The cardiac, renal and vascular responses increase the workload of the heart, further accelerating myocardial damage and exacerbating the heart failure state. Accordingly, it is desirable to reduce the level of sympathetic nervous system and other neurohormonal activation in order to stop or at least minimize this vicious cycle and thereby treat or manage the heart failure.

A number of drug treatments have been proposed for the management of hypertension, heart failure and other cardiovascular and renal disorders. These include vasodilators to reduce the blood pressure and ease the workload of the heart, diuretics to reduce fluid overload, inhibitors and blocking agents of the body's neurohormonal responses, and other medicaments.

Various surgical procedures have also been proposed for these maladies. For example, heart transplantation has been proposed for patients who suffer from severe, refractory heart failure. Alternatively, an implantable medical device such as a ventricular assist device may be implanted in the chest to increase the pumping action of the heart. Alternatively, an intra-aortic balloon pump may be used for maintaining heart function for short periods of time, but typically no longer than one month. Other surgical procedures are available as well.

Although each of these alternative approaches is beneficial in some ways, each of the therapies has its own disadvantages. For example, drug therapy is often incompletely effective. Some patients may be unresponsive (refractory) to medical therapy. Drugs often have unwanted side effects and may need to be given in complex regimens. These and other factors contribute to poor patient compliance with medical therapy. Drug therapy may also be expensive, adding to the health care costs associated with these disorders. Likewise, surgical approaches are very costly, may be associated with significant patient morbidity and mortality and may not alter the natural history of the disease. Accordingly, there continues to be a substantial and long felt need for new devices and methods for treating and/or managing high blood pressure, heart failure and renal disease, as well as their associated complications.

SUMMARY OF THE INVENTION

The present invention provides a number of devices, systems and methods by which the real or apparent renovascular perfusion and the renal interstitial hydrostatic pressure may be selectively and controllably increased. By selectively and controllably increasing renovascular perfusion and interstitial hydrostatic pressure when the heart is unable to pump sufficient blood or when renal perfusion is otherwise suboptimal, the renal system does not experience the reduced perfusion. Because the renal system does not experience the reduced perfusion, it does not initiate or contribute to, and may reduce the neurohormonal activation normally caused by reduced cardiac output and suboptimal renal perfusion, nor does it begin or continue, and could reverse the process of sodium and water retention that also would otherwise result. Thus, by selectively and controllably increasing renovascular perfusion during periods of decreased cardiac output or suboptimal renal perfusion, the present invention reduces or reverses neurohormonal activation and fluid retention, and thereby minimizes their deleterious effects on the heart, vasculature, kidneys and other body systems.

In the case of end stage renal disease (ESRD), the present invention provides a number of devices, systems and methods by which renal perfusion and pressure can be increased, thereby restoring or augmenting perfusion of the kidney and blood filtration. In addition, by increasing renal perfusion, the present invention increases interstitial pressure to reduce sodium and water reabsorption, which have been shown to be interrelated.

In an exemplary embodiment, the present invention provides a method of treating a patient utilizing a blood perfusion modification device, one or more physiologic sensors, and a control system. The blood perfusion modification device may be positioned in the renovascular circulation or immediately adjacent thereto. The sensor is preferably positioned in a renal artery or upstream thereof, but may also be placed in, on or adjacent the patient to generate a signal indicative of the need to modify renal perfusion. For example, the sensor may be positioned in a kidney, a renal artery or vein or adjacent thereto to generate a signal indicative of arterial blood perfusion, renal venous pressure or renal interstitial pressure. The blood perfusion modification device may be activated, deactivated or otherwise modified as a function of the sensor signal to cause or simulate a change, and preferably an increase, in renal perfusion and/or pressure. This method may be used to treat a number of clinical conditions including congestive heart failure, hypertension, renal failure, cardiovascular abnormalities, and the like. In each instance, the method may include the initial step of diagnosing or monitoring the clinical condition or a symptom or sign thereof, and thereafter providing treatment as needed.

The present invention also provides a system including a blood perfusion modification device (e.g., a flow regulator, a flow redirector or a pump), a physiologic sensor (e.g., a transducer or a gauge), and a control system operably connected to both. The blood perfusion modification device is preferably positioned in the renovascular circulation. The control system (or a portion thereof) may be implanted or carried externally by the patient. In the closed-loop mode, the sensor generates a sensor signal indicative of the need to modify renovascular perfusion, and the control system generates a control signal to activate the modification device as a function of the sensor signal to thereby modify the renovascular circulation. In the open-loop mode, which may or may not utilize feedback from the sensor, the control system generates a control signal to activate the modification device as dictated by, for example, a pre-programmed algorithm, the patient or the physician.

The sensor may comprise, for example, a piezoelectric pressure transducer, an ultrasonic flow velocity transducer, a thermodilution flow transducer, or a strain gauge. As such, the sensor may generate a signal indicative of pressure (e.g., mean, systolic, diastolic or pulse), blood flow velocity, vasoactivity, or other fluid dynamic property. Alternatively, the sensor may measure the blood concentration of a component (e.g., sodium, renin, etc.) or an arterial/venous difference in concentration of the component.

The blood perfusion modification device may comprise a flow regulator positioned in a renal vein or immediately downstream thereof to create backpressure in. the renovascular circulation. Alternatively, the blood perfusion modification device may comprise a flow redirector positioned downstream of a renal artery to redirect blood flow to the renal artery. As a further alternative, the blood perfusion modification device may comprise a pump. The pump may be positioned upstream of a renal artery to supplement blood flow to the renal artery or positioned downstream of a renal vein to supplement blood flow from the renal vein. As yet a further alternative, the blood perfusion modification device may comprise a drug delivery device. In each of these embodiments, the blood perfusion modification device may be positioned intravascularly or extravascularly. By way of example, not limitation, the blood perfusion modification device may comprise an inflatable cuff, a rotatable ring, a hydraulic piston, a solenoid, an inflatable balloon, or a drug delivery device.

The control system may include a processor and memory. The memory may include software containing one or more algorithms defining one or more functions or relationships between the control signal and the sensor signal. The algorithm may dictate activation or deactivation control signals depending on the sensor signal or a mathematical derivative thereof. The algorithm may dictate an activation or a deactivation control signal when the sensor signal falls below a lower predetermined threshold value, rises above an upper predetermined threshold value or when the sensor signal indicates a specific physiologic event.

BRIEF DESCRIPTION OF THE DRAWINGS

FIGS. 6A and 6B are side cross-sectional schematic illustrations of an extraluminal flow regulator/redirector in the form of an inflatable cuff in accordance with the present invention, shown in the deactivated (unconstricted) and activated (constricted) states, respectively;

FIGS. 7A and 7B are side cross-sectional schematic illustrations of an intraluminal flow regulator/redirector in the form of an inflatable balloon in accordance with the present invention, shown in the deactivated (unconstricted) and activated (constricted) states, respectively;

FIG. 10 is a side cross-sectional schematic illustration of an extraluminal flow supplementor/pump in the form of a series of balloons or solenoids in accordance with the present invention, shown in the deactivated (unconstricted) state;

FIG. 11 is a side cross-sectional schematic illustration of an intraluminal flow supplementor/pump in the form of an impeller in accordance with the present invention.

DETAILED DESCRIPTION OF THE PREFERRED EMBODIMENTS

The following detailed description should be read with reference to the drawings in which similar elements in different drawings are numbered the same. The drawings, which are not necessarily to scale, depict illustrative embodiments and are not intended to limit the scope of the invention.

Figure 1:
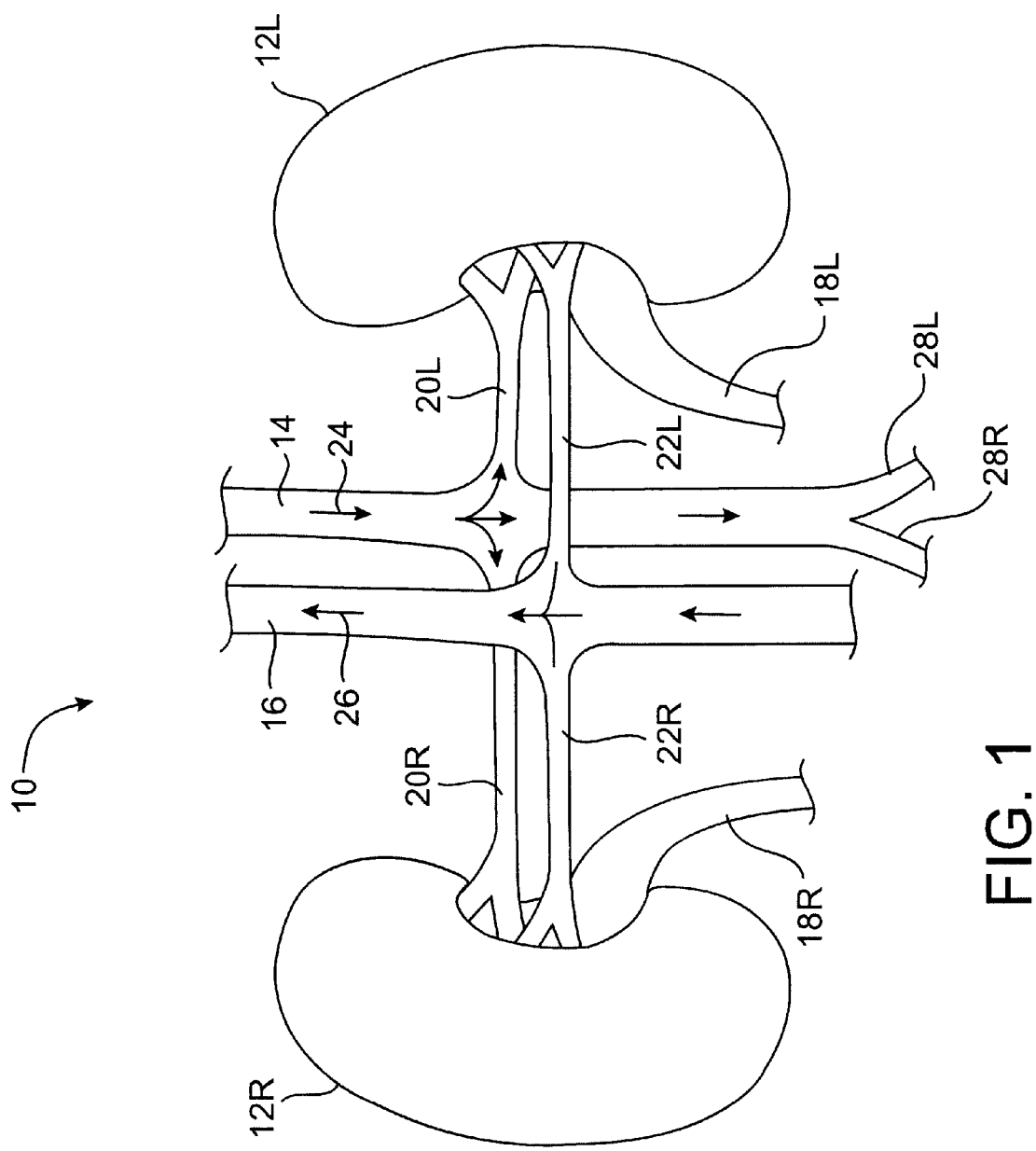
FIG. 1 is a schematic illustration of the renovasculature and associated anatomy.

Refer now to FIG. 1 which is a schematic illustration of the renal system 10 of an adult human. The right and left sides of the renal system 10 are substantially symmetrical and are identified by the letters R and L, respectively. Blood is supplied to the kidneys 12 by way of the descending aorta 14 and the renal arteries 20. Blood is removed from the kidneys 12 by way of the inferior vena cava 16 and the renal veins 22. The descending aorta 14 bifurcates downstream into the common iliac arteries 28. The direction of the arterial blood flow in the descending aorta 14 is indicated by arrows 24, and the direction of the venous blood flow in the inferior vena cava 16 is indicated by arrows 26. Waste products are removed from the blood by the kidneys 12 and transported to the bladder (not shown) by way of ureters 18.

As stated previously, a number of body systems are activated to compensate for the heart's inability to pump sufficient blood or in the presence of renal disease or restricted renal perfusion (e.g., renal artery stenosis causing hypertension and/or renal disease). In the case of heart failure, the renal system 10 senses the heart's inability to pump sufficient blood by decreased blood perfusion (flow, pressure, etc.) in the renal arteries 20 and other parts of the renovasculature. The renal system 10 responds to this condition by initiating or contributing to a neurohormonal sequence that signals the heart to increase heart rate and force of contraction to increase the cardiac output, signals the kidneys to expand the blood volume by retaining sodium and water, and it signals the arterioles to constrict to elevate the blood pressure. The cardiac, renal and vascular responses increase the workload of the heart, further accelerating myocardial damage and exacerbating the heart failure state. To address this problem, the present invention basically provides a number of devices, systems and methods by which the renal system 10 experiences normal or supranormal perfusion even in the face of reduced cardiac output and/or vasoconstriction. By maintaining or augmenting renal perfusion, the renal system 10 including renal baroreceptors and the juxtaglomerular apparatus are not activated, and the viscous cycle referred to above may be stopped or at least moderated.

In the case of end stage renal disease (ESRD), the kidney has often undergone substantial scarring and fibrosis. Thus, perfusion of the kidney and filtration of the blood are limited. The present invention provides a number of devices, systems and methods by which renal perfusion and pressure can be increased, thereby restoring or augmenting perfusion of the kidney and blood filtration. In addition, by increasing renal perfusion, the present invention increases interstitial pressure to reduce sodium and water reabsorption, which have been shown to be interrelated.

With reference to FIGS. 2–5, the present invention generally provides a system including a physiologic sensor 30 (e.g., a transducer or a gauge), a blood perfusion modification device 50, 60, 70 and/or 80 (e.g., a flow regulator, a flow redirector or a pump), and a control system 40. As used herein, perfuision, blood perfusion and renal perfusion generally refer to a fluid dynamic property of blood flow such as volumetric flow rate, flow velocity and/or pressure including absolute, mean or pulse pressure, or a fluid static property such as interstitial pressure. The sensor 30 senses and/or monitors one or more fluid dynamic properties of blood flow or renal pressure or function and is generically referred to herein as a sensor. Similarly, the blood perfusion modification devices 50, 60, 70, 80 modify one or more fluid dynamic properties of blood flow and are generically referred to herein as modification devices. In each embodiment, the connections between the components 30/40/50/60/70/80 may be physical (e.g., wires, tubes, cables, etc.) or remote (e.g., transmitter/receiver, inductive, magnetic, etc.). For physical connections, the connection may travel intraarterially, intravenously, intra-abdominally, subcutaneously, or through other natural tissue paths.

The need to preserve or augment renal blood perfusion or pressure may be, for example, detected by the sensor 30, which may be placed in one or both renal arteries 20, the descending aorta 14, or upstream thereof, within the kidney itself or in the urinary bladder. The control system 40 generates a control signal as a function of the received sensor signal. The control signal activates, deactivates or modifies one or more parameters of the blood perfusion modification device 50, 60, 70, 80. Thus, when the sensor 30 detects a reduction in cardiac output, the control system 40 generates an activation control signal to activate the blood perfusion modification device 50, 60, 70, 80 thereby increasing renovascular perfusion such that the renal system 10 does not experience reduced perfusion. When the sensor 30 detects improvement or normalization in the sensed parameter, the control system 40 generates a control signal to deactivate or otherwise modify the activity of the blood perfusion modification device 50, 60, 70, 80.

With continued reference to FIGS. 2–5, the sensor 30 is operably coupled to the control system 40 by electric sensor cable or lead 32. The sensor 30 may comprise any suitable device that measures a fluid dynamic property of blood flow or other parameter(s) of interest which is (are) indicative of the need to modify (i.e., increase) renal perfusion. For example, the sensor 30 may comprise a transducer or gauge that measures blood pressure (systolic, diastolic, pulse or average pressure), blood volumetric flow rate, blood flow velocity, etc. Alternatively, the sensor 30 may comprise a transducer or gauge that measures urine production (e.g., volumetric), composition or concentration, a change in any of which may be indicative of the need to modify renal perfusion. Examples of suitable transducers or gauges for the sensor 30 include a piezoelectric pressure transducer, an ultrasonic flow velocity transducer, an ultrasonic volumetric flow rate transducer, a thermodilution flow velocity transducer, and a capacitive pressure transducer. Although only one sensor 30 is shown, multiple sensors 30 of the same or different type at the same or different location may be utilized.

In this embodiment, the sensor 30 is preferably positioned on the arterial side of the renal vasculature. In particular, the sensor 30 may be located in or on one or both kidneys 12, renal arteries 20, the descending aorta 14, or upstream thereof, such that suboptimal renal perfusion may be readily ascertained. The sensor may alternatively be implanted in the bladder to measure urine production. The sensor 30 may be mounted intravascularly or extravascularly, depending on the type of transducer or gauge utilized.

With continued reference to FIGS. 2–5, control system 40 includes a control block 41 comprising a processor 43 and a memory 42. Control system 40 is connected to the sensor 30 by way of sensor cable 32. Control system 40 is also connected to the blood perfusion modification device 50, 60, 70, 80 by way of electric control cable 38. Thus, the control system 40 receives a sensor signal (also referred to as a transducer signal) from the sensor 30 by way of sensor cable 32, and transmits a control signal to the blood perfusion modification device 50, 60, 70, 80 by way of control cable 38.

The memory 42 may contain data related to the sensor signal, the control signal, and/or values and commands provided by the input device 44. The memory 42 may also include software containing one or more algorithms defining one or more functions or relationships between the control signal and the sensor signal. The algorithm may dictate activation, deactivation or modification control signals depending on the sensor signal or a mathematical derivative thereof. For example, the algorithm may dictate an activation control signal when the sensor signal falls below a lower predetermined threshold value. The algorithm may also dictate a deactivation control signal when the sensor signal rises above an upper predetermined uphold threshold value.

The following predetermined threshold values are provided by way of example, not limitation. If the sensor signal is indicative of systolic pressure, the lower threshold value may be approximately 80 mm Hg and the upper threshold value may be approximately 120 mm Hg. If the sensor signal is indicative of diastolic pressure, the lower threshold value may be approximately 60 mm Hg and the upper threshold value may be approximately 80 mm Hg. If the sensor signal is indicative of mean pressure, the lower threshold value may be approximately 70 mm Hg and the upper threshold value may be approximately 110 mm Hg. If the sensor signal is indicative of flow rate, the lower threshold value may be approximately 500 ml/min and the upper threshold value may be approximately 700 ml/min for each kidney. In essence, the algorithm dictates activation or deactivation of the blood perfusion modification device 50, 60, 70, 80 to thereby increase or decrease real or apparent renovascular perfusion by instigating a control signal transmission as a function of the sensor signal.

The control system 40 may operate as a closed loop utilizing feedback from the sensor 30, or as an open loop utilizing commands received by input device 44. The open loop operation of the control system 40 preferably utilizes some feedback from the sensor 30, but may also operate without feedback. Commands received by the input device 44 may directly influence the control signal or may alter the software and related algorithms contained in memory 42. The patient and/or treating physician may provide commands to input device 44. Display 45 may be used to view the sensor signal and/or the software contained in memory 42.

The control signal generated by the control system 40 may be continuous, periodic, episodic or a combination thereof, as dictated by a preset or programmable algorithm contained in memory 42. Continuous control signals include a constant pulse, a constant sequence of pulses, a triggered pulse and a triggered sequence of pulses. Examples of periodic control signals include each of the continuous control signals described above which have a designated start time (e.g., beginning of each minute, hour or day) and a designated duration (e.g., 1 second, 1 minute, 1 hour). Examples of episodic control signals include each of the continuous control signals described above which are triggered by an episode (e.g., activation by the patient/physician, an increase in blood pressure above a certain threshold, ECG, etc).

The control system 40 may be implanted in whole or in part. For example, the entire control system 40 may be carried externally by the patient utilizing transdermal connections to the sensor lead 32 and the control lead 38. Alternatively, the control block 41 may be implanted with the input device 44 and display 45 carried externally by the patient utilizing transdermal connections therebetween. As a further alternative, the transdermal connections may be replaced by cooperating transmitters/receivers to remotely communicate between components of the control system 40 and/or the sensor 30 and blood perfusion modification device 50, 60, 70, 80. If all of the components are implanted, the inter-component connections may be eliminated.

Figure 2:
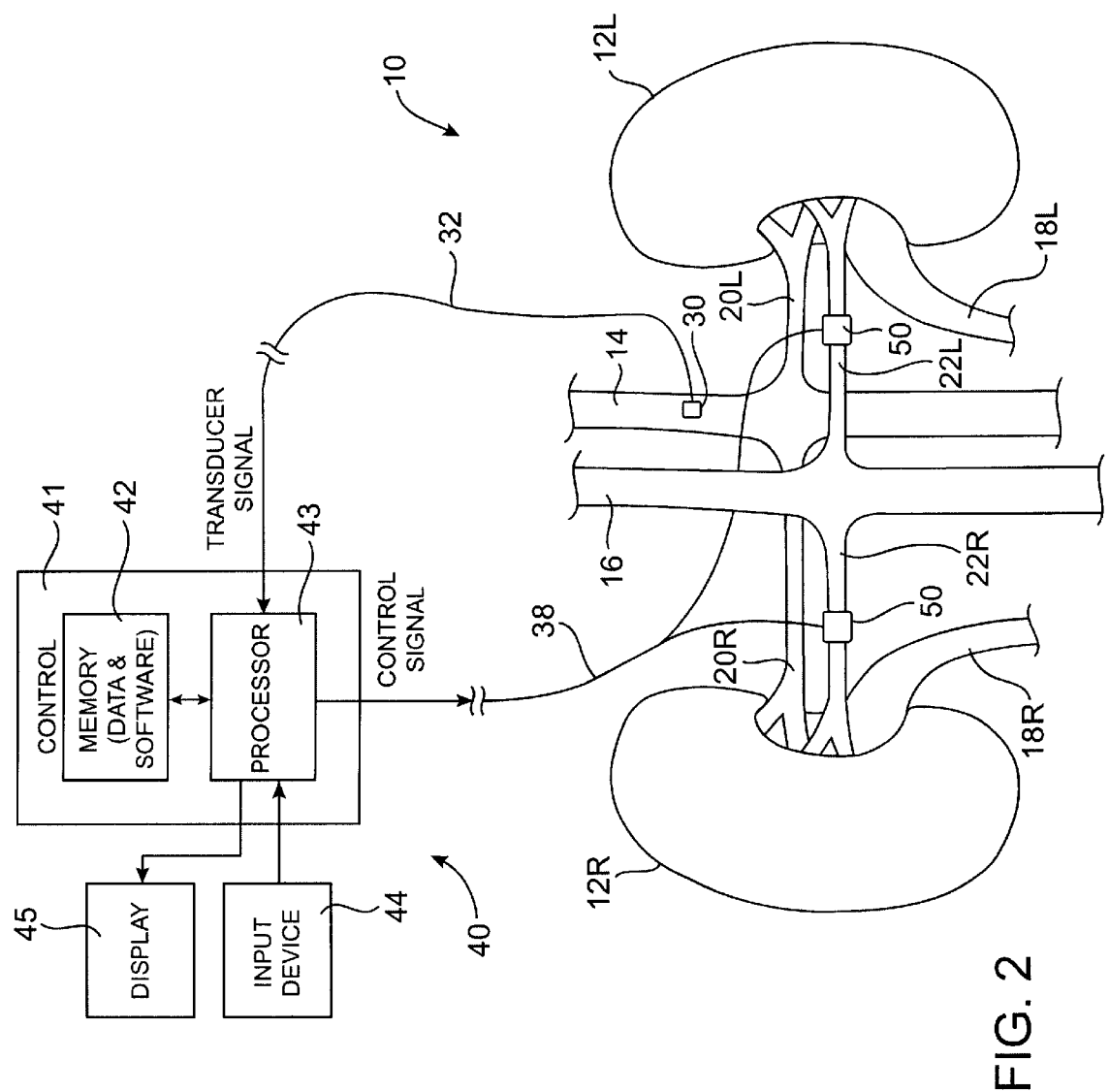
FIG. 2 is a schematic illustration of a renal vein flow regulator system in accordance with the present invention.

Refer now to FIG. 2 which schematically illustrates a renal vein flow regulator 50 in accordance with an embodiment of the present invention. The flow regulator 50 may be intravascularly or extravascularly positioned in or on one or both renal veins 22 or downstream thereof on the inferior vena cava 16. Flow regulator 50 may be activated or deactivated by a control signal received from control cable 38. When activated, the flow regulator 50 constricts the renal vein 22 or otherwise reduces the cross-sectional area of the lumen therein to create back pressure in the renovasculature, thereby increasing blood and interstitial pressure in the renal tissues. By creating back pressure in the renal tissues during episodes of reduced renal perfusion, the renal system 10 does not perceive the reduction in perfusion.

Figure 3:
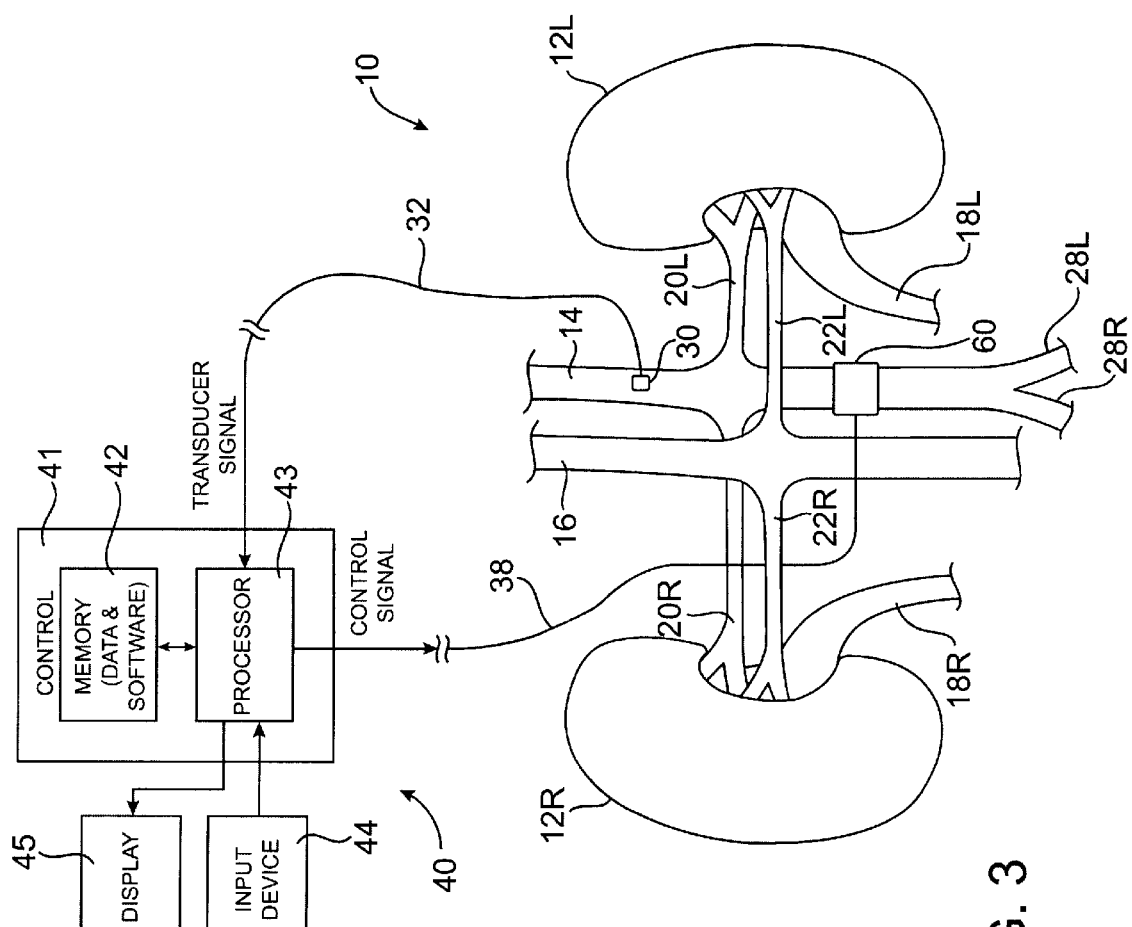
FIG. 3 is a schematic illustration of a flow redirection system in accordance with the present invention.

Refer now to FIG. 3 which schematically illustrates a flow redirector 60 in accordance with another embodiment of the present invention. The flow redirector 60 may be intravascularly or extravasculary positioned in or on the descending aorta 14 downstream of the renal arteries 20, or in or on one or both of the common iliac arteries 28. The flow redirector 60 may be activated or deactivated by a control signal received from control cable 38. When activated, the flow redirector 60 constricts the descending aorta or otherwise reduces the size of the lumen therein to redirect flow to the renal arteries 20 thereby increasing renovascular perfusion. By artificially increasing renovascular perfusion during a state of reduced cardiac output, renal artery constriction or renal artery stenosis, renal perfusion is preserved or enhanced. Preferably, the flow redirector 60 would be activated in such a manner as to minimize the effects on downstream perfusion into the lower extremities.

Figure 4:
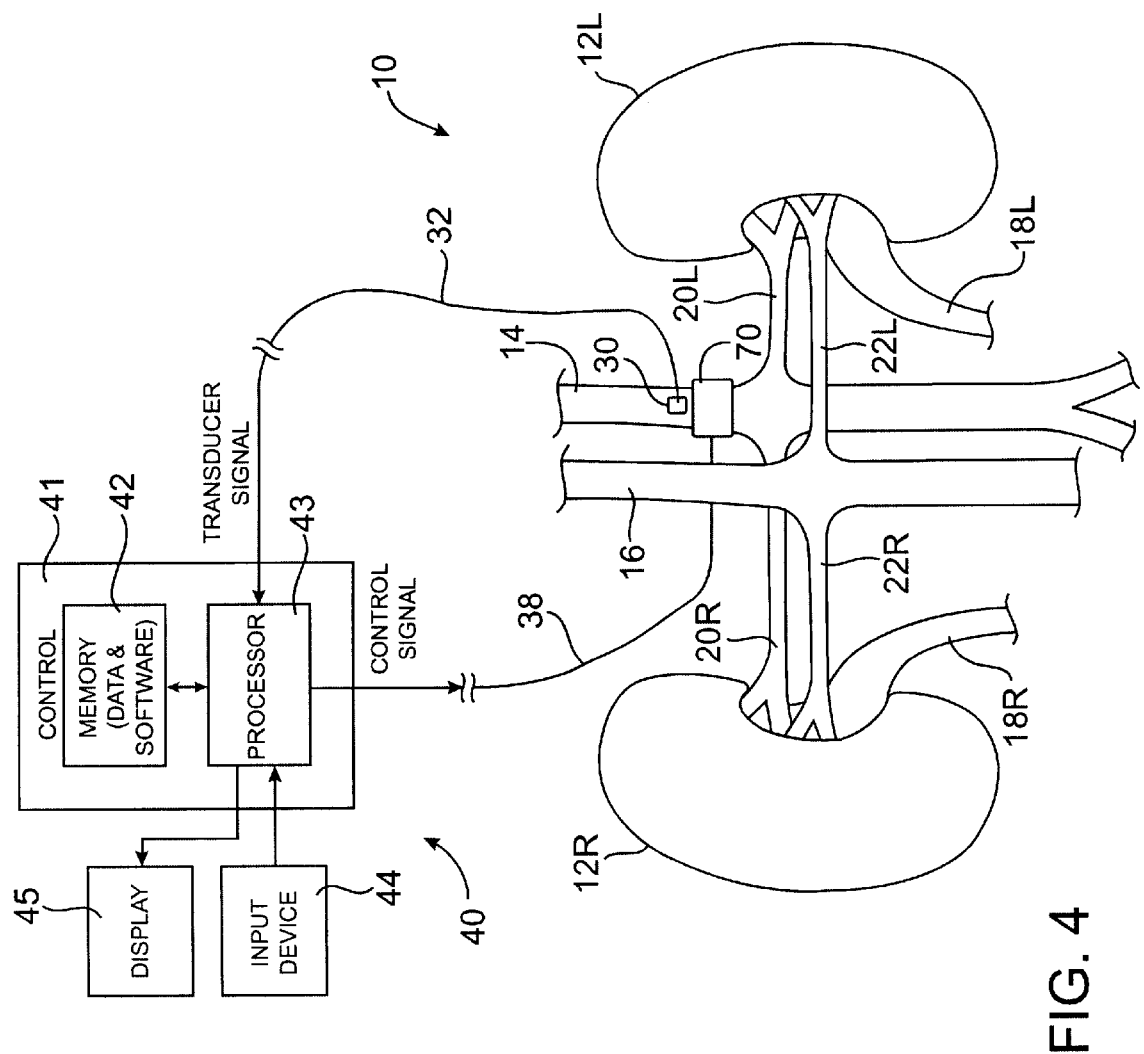
FIG. 4 is a schematic illustration of an arterial flow pump system in accordance with the present invention.

Refer now to FIG. 4 which schematically illustrates an arterial blood flow pump 70 in accordance with another embodiment of the present invention. The arterial flow pump 70 may be positioned intravascularly or extravascularly in or on the descending aorta 14 upstream of the renal arteries 20 or in the renal arteries 20. The arterial flow pump 70 may be activated and deactivated by a control signal received from control cable 38. When activated, the arterial flow pump 70 supplements arterial blood flow to the renal arteries 20 thereby increasing renal perfusion.

Figure 5:
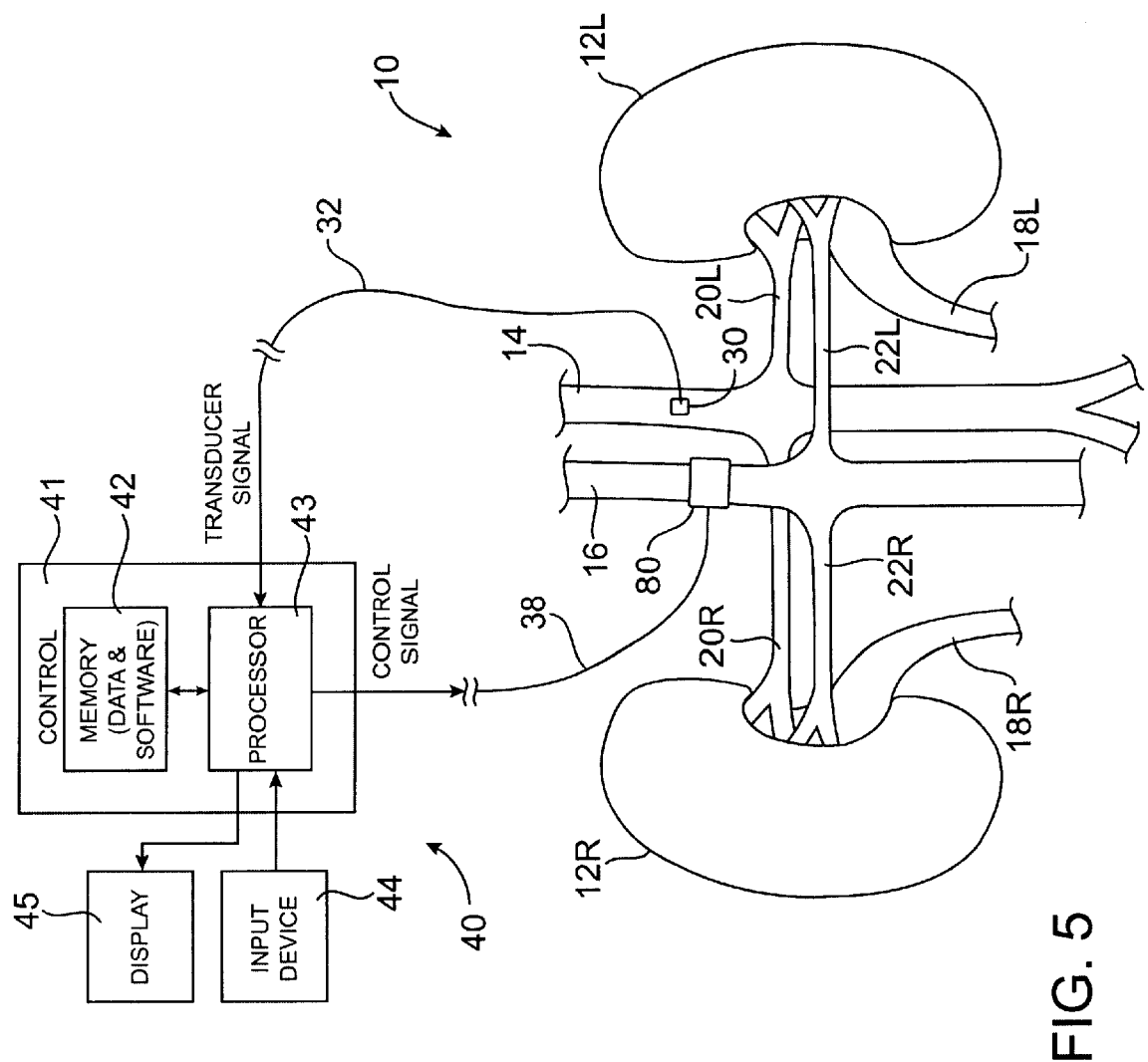
FIG. 5 is a schematic illustration of a venous flow pump system in accordance with the present invention.

Refer now to FIG. 5 which schematically illustrates a venous blood flow pump 80 in accordance with another embodiment of the present invention. Venous flow pump 80 may be intravascularly or extravascularly may be positioned in or on the renal veins 22, or in or on the inferior vena cava 16 downstream of the renal veins 22. The venous flow pump 80 may be activated and deactivated by a control signal received from control cable 38. When activated, the venous flow pump 80 reduces blood flow or causes back flow in the renal veins 22 thereby increasing renal back pressure.

Refer now to FIGS. 6–12 which illustrate various embodiments of flow regulators, flow redirectors and pumps that may be utilized for the blood perfusion modification devices 50, 60, 70, 80 described with reference to FIGS. 2–5. Each of FIGS. 6–12 schematically illustrate intravascular or extravascular devices disposed in or on a generic vessel 90 having a vascular wall 92 and a vascular lumen 94. The vessel 90 generically refers to the portion of the vasculature in or on which the blood perfusion modification device 50, 60, 70, 80 is positioned as described previously. Each of the illustrations of FIGS. 6–12 are longitudional cross-sectional views unless otherwise specified and are generally circular in lateral cross-section unless otherwise specified.

Refer now specifically to FIGS. 6A and 6B which show side cross-sectional schematic illustrations of an external inflatable cuff 100 in accordance with an embodiment of the present invention. FIG. 6A illustrates the inflatable cuff 100 in the deactivated (unconstricted) state, and FIG. 6B illustrates the inflatable cuff 100 in the activated (constricted) state. The inflatable cuff 100 may be used for the renal vein flow regulator 50 as illustrated in FIG. 2 or the flow redirector 60 illustrated in FIG. 3. Those skilled in the art will recognize the inflatable cuff 100 illustrated is merely schematic and is intended to generically refer to a wide variety of inflatable cuffs. Examples of inflatable cuffs that may be adapted for use in the present invention are disclosed in U.S. Pat. No. 4,256,094 to Kapp et al. and U.S. Pat. No. 4,881,939 to Newman, the entire disclosures of which are hereby incorporated by reference.

Inflatable cuff 100 includes a housing 102 which may be connected to the vessel wall 92 utilizing conventional techniques such as sutures 104. Housing 102 contains an inflatable annular balloon 106 having an interior 107 which is in fluid communication with a fluid line 108. The balloon 106 may be an annular geometry with a central passageway to accommodate the vessel 90 therein as illustrated, or may be a geometry without a passageway and reside on one side of the vessel 90. In addition, one balloon 106 may be utilized as shown, or a plurality of balloons 106 may be utilized.

A pressure/vacuum source 110 (e.g., a closed volume piston pump) selectively inflates and deflates the balloon 106 by way of pressure line 108. The pressure/vacuum source 110 is preferably implanted, but may be carried externally by the patient with a transdermal connection to the pressure line 108. A saline liquid inflation fluid is preferred, but other fluids (i.e. liquids and gases) may be used.

The pressure/vacuum source 110 is connected to the control cable 38, which provides a control signal from control system 40 to activate or deactivate the pressure/vacuum source 110 and thereby inflate or deflate the balloon 106. When activated, the pressure/vacuum source 110 applies pressure and causes the balloon 106 to inflate thereby constricting the vascular wall 92 and obstructing or reducing the size of the internal lumen 94. The internal lumen 94 may be partially or totally occluded by controlling the degree of balloon 106 inflation. When deactivated, the pressure/vacuum source 110 applies vacuum and causes the balloon 106 to deflate thereby permitting the vascular wall 92 to return to its unconstricted state and restoring the nominal size of the internal lumen 94.

The pressure/vacuum source 110 may be automatically actuated by the control system 40 as discussed above, or may be manually actuated. An example of an externally manually actuated pressure/vacuum source is disclosed in U.S. Pat. No. 4,709,690 to Haber, the entire disclosure of which is hereby incorporated by reference. Examples of transdermally manually actuated pressure/vacuum sources are disclosed in U.S. Pat. No. 4,586,501 to Claracq, U.S. Pat. No. 4,828,544 to Lane et al., and U.S. Pat. No. 5,634,878 to Grundei et al., the entire disclosures of which are hereby incorporated by reference.

In use, the sensor 30 detects a reduction in renal perfusion or other change indicative of the need to activate the system as indicated by a sensor signal transmitted by way of sensor cable 32 to the control system 40. In response, the control system 40 transmits a control signal as a function the sensor signal as dictated by the algorithm contained in memory 42. The control signal is transmitted by way of control cable 38 to the pressure/vacuum source 110. Depending on the control signal, the pressurized fluid source 110 is activated (pressure) or deactivated (vacuum) to inflate or deflate the balloon 106.

If the inflatable cuff 100 is utilized as a renal vein flow regulator 50 as illustrated in FIG. 2, the reduced size of the vascular lumen 94 causes back pressure in the renal veins 22 and ultimately the renal parenchyma and arterial circulation thereby causing an apparent increase in renovascular perfusion and pressure. If the inflatable cuff 100 is utilized as a flow redirector 60 as illustrated in FIG. 3, the reduced size of the vascular lumen 94 causes blood to be redirected into the renal arteries 20 thereby causing an increase in renovascular perfusion. In either instance, renovascular perfusion and/or intrarenal pressure are maintained or augmented.

Inflatable cuff 100 is one example of many different mechanisms for applying external compression to the vascular wall 92 to reduce the size of the internal lumen 94. Other mechanisms for applying for external compression to the vascular wall 92 are described in greater detail with reference to FIGS. 8A, 8B, 9A and 9B. In addition to the specific mechanisms mentioned herein, those skilled in the art will recognize that many other mechanisms may be adapted for this application. For example, external compression may be applied utilizing an electromagnetically actuated ferro-fluid device as disclosed in the U.S. Pat. No. 5,509,888 to Miller, the entire disclosure of which is hereby incorporated by reference. Another example of an electromagnetically actuated ferro-fluid type external compression device is disclosed in U.S. Pat. No. 4,053,952 to Goldstein, the entire disclosure of which is incorporated by reference.

Refer now to FIGS. 7A and 7B which show cross-sectional schematic illustrations of an internal inflatable balloon device 200 in accordance with another embodiment of the present invention. FIG. 7A illustrates the inflatable balloon device 200 in the deactivated (unconstricted) state, and FIG. 7B illustrates the inflatable balloon device 200 in the activated (constricted) state. The inflatable balloon device 200 may be used for the renal vein flow regulator 50 illustrated in FIG. 2 or the flow redirector 60 illustrated in FIG. 3.

Those skilled in the art will recognize that the internal inflatable balloon device 200 is merely schematic and is intended to generically refer to a wide variety of internal occlusion devices. An example of an internal inflatable balloon device that may be adapted for use in the present invention is disclosed in U.S. Pat. No. 4,682,583 to Burton et al., the entire disclosure of which is hereby incorporated by reference. Another example of an internal inflatable balloon device that may be adapted for use in the present invention is disclosed in U.S. Pat. No. 5,634,878 to Grandei et al., the entire disclosure of which is hereby incorporated by reference.

Inflatable balloon device 200 includes a housing 202 which may be connected to the inside surface of the vessel wall 92 utilizing conventional techniques such as those used for implanting vascular stents, grafts and filters. Housing 202 includes an inflatable annular balloon 206 having an interior 207 which is in fluid communication with a fluid line 208. The balloon 206 may be an annular geometry with a central perfusion passageway as illustrated, or may be a geometry without a passageway and reside on one side of the vessel 90. In addition, one balloon 206 may be utilized as shown, or a plurality of balloons 206 may be used.

A pressure/vacuum source 110 selectively inflates and deflates the balloon 206 by way of pressure line 208. The pressure/vacuum source 110 is connected to the control cable 38, which provides a control signal from control system 40 to activate or deactivate the pressure/vacuum source 110 and thereby inflate or deflate the balloon 206. When activated, the pressure/vacuum source 110 applies pressure and causes the balloon 206 to inflate thereby obstructing or reducing the size of the internal lumen 94. The internal lumen 94 may be partially or totally occluded by adjusting the degree of balloon 206 inflation. When deactivated, the pressure/vacuum source 110 applies vacuum and causes the balloon 206 to deflate thereby restoring the nominal size of the internal lumen 94. The internal inflatable balloon device 200 basically operates on the same principles as the external compression device 100 described previously, except that inflatable balloon device 200 does not utilize external compression, but rather totally or partially occludes the vascular lumen 94 without affecting the vascular wall 92.

Figure 8B:
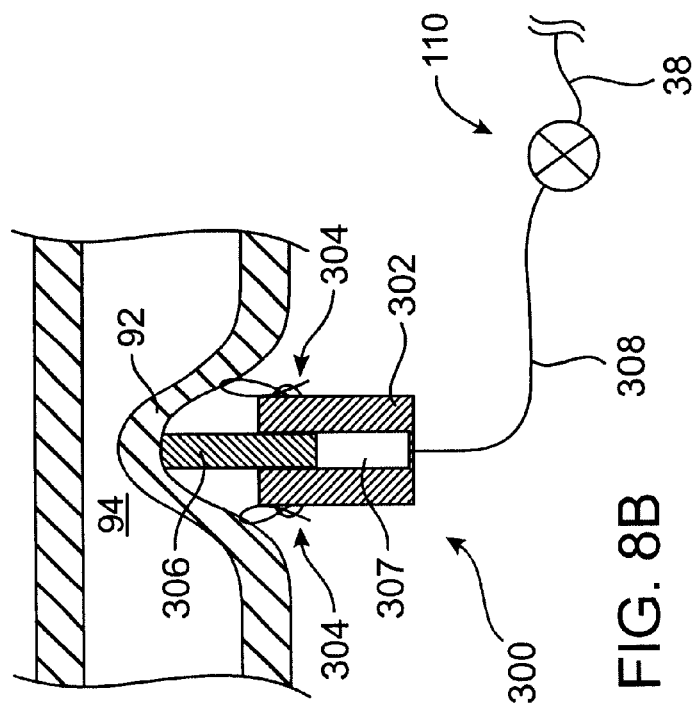
FIGS. 8A and 8B are side cross-sectional schematic illustrations of an extraluminal flow regulator/redirector in the form of a hydraulic piston or solenoid in accordance with the present invention, shown in the deactivated (unconstricted) and activated (constricted) states, respectively.
Figure 8A:
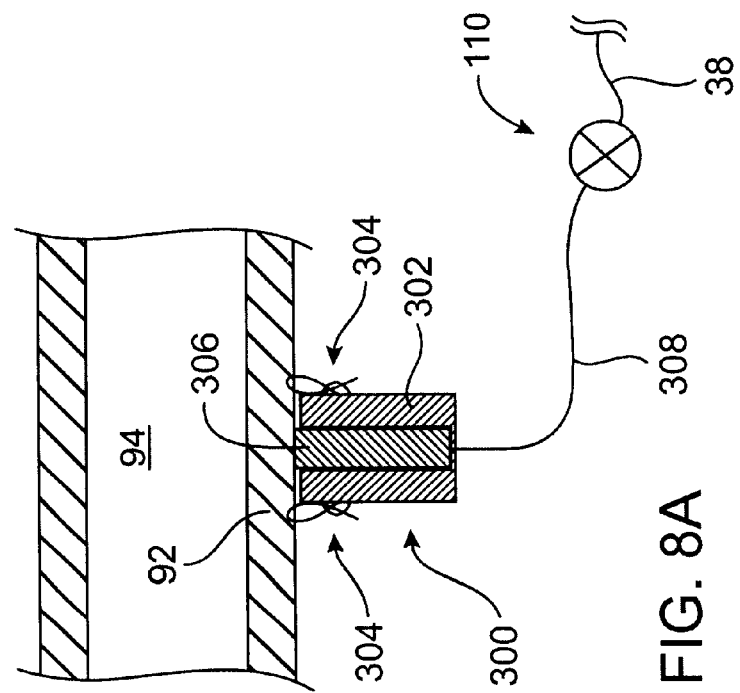

Refer now to FIGS. 8A and 8B which show side cross-sectional schematic illustrations of a piston device 300 in accordance with another embodiment of the present invention. FIG. 8A illustrates the piston device 300 in the deactivated (unconstricted) state, and FIG. 8A illustrates the piston device 300 in the activated (constricted) state. The piston device 300 may be used for the renal vein flow regulator 50 illustrated in FIG. 2 or the flow redirector 60 illustrated in FIG. 3. Those skilled in the art will recognize that the piston device 300 illustrated is merely schematic and is intended to generically refer to a wide variety of piston type devices. An example of a piston type device that may be adapted for use in the present invention is disclosed in U.S. Pat. No. 4,014,318 to Dockum et al., the entire disclosure of which is hereby incorporated by reference.

Piston device 300 includes a housing 302 which may be connected to the vessel wall 92 utilizing conventional techniques such as sutures 304. Housing 302 includes an internal chamber 307 in which piston 306 is slidably disposed. The internal chamber 307 is in fluid communication with a fluid line 308. A pressure/vacuum source 110 selectively fills an empties the chamber 307 by way of pressure line 308. The pressure/vacuum source 110 is connected to the control cable 38, which provides a control signal from control system 40 to activate or deactivate the pressure/vacuum source 110.

When activated, the pressure/vacuum source 110 fills the internal chamber 307 with fluid thereby displacing the piston 306 to constrict the vascular wall 92 and reduce the size of the internal lumen 94. The internal lumen 94 may be partially or totally occluded by adjusting the displacement distance of the piston 306. When deactivated, the pressure/vacuum source 110 empties the internal chamber 307 causing the piston 306 to be displaced back into the chamber 307 thereby permitting the vascular wall 92 to return to its unconstricted state and restoring the nominal size of the internal lumen 94. The function and use of the piston device 300 is otherwise essentially the same as the other external compression device 100 discussed previously.

As illustrated and described, the piston device 300 operates by hydraulic actuation. Alternatively, the piston device 300 may operate by electromagnetic actuation such as provided by a solenoid device. An example of an electromagnetic solenoid device is disclosed in Dockum et al. '318 mentioned previously. If electromagnetic actuation is utilized, the pressure/vacuum source 110 may be replaced by a suitable amplifier to power the electromagnets in the solenoid. The function and use of the solenoid alternative is otherwise essentially the same as the hydraulic embodiment discussed above.

Figure 9B:
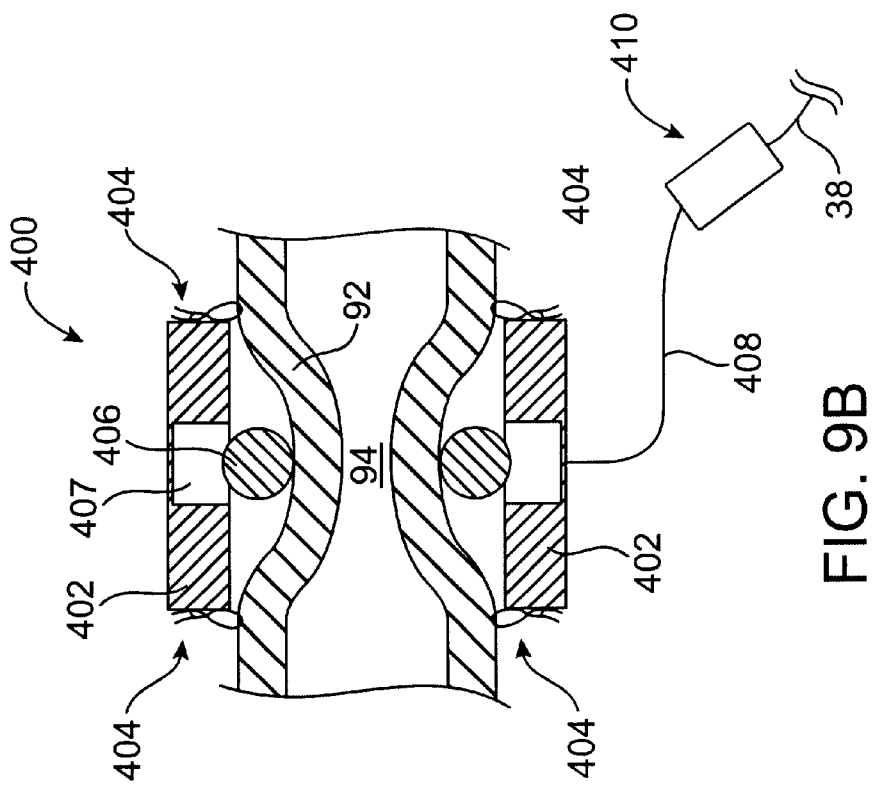
FIGS. 9A and 9B are side cross-sectional schematic illustrations of an extraluminal flow regulator/redirector in the form of a rotatable ring in accordance with the present invention, shown in the deactivated (unconstricted) and activated (constricted) states, respectively.
Figure 9A:
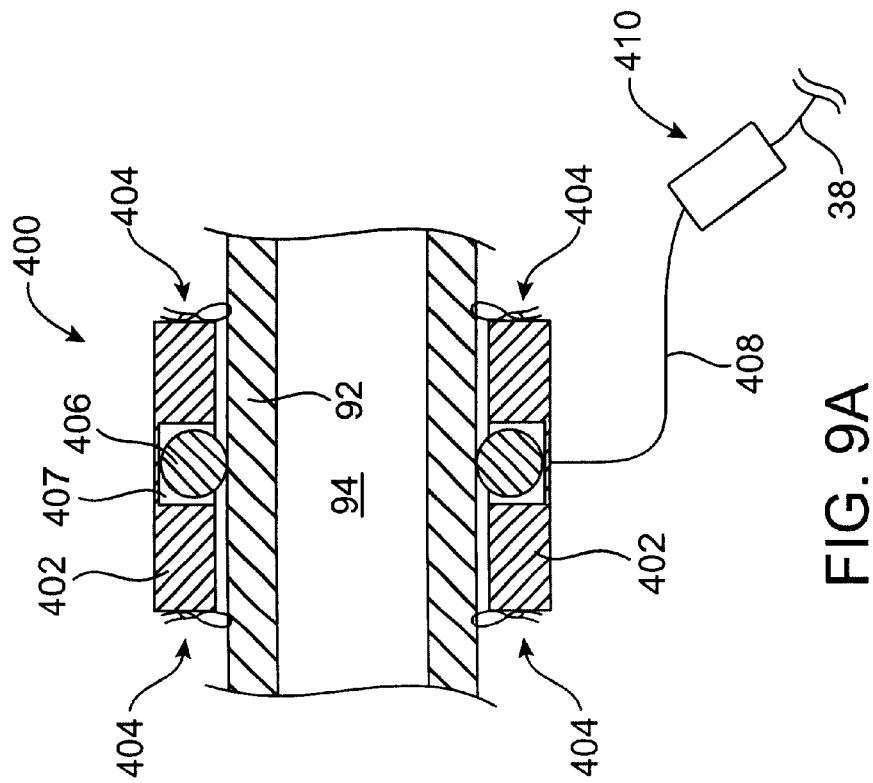

Refer now to FIGS. 9A and 9B which show side cross-sectional schematic illustrations of a rotatable ring device 400 in accordance with another embodiment of the present invention. FIG. 9A illustrates the rotatable ring device 400 in the deactivated (unconstricted) state and FIG. 9B illustrates the rotatable ring device 400 in the activated (constricted) state. The rotatable ring device 400 may be used for the renal vein flow regulator 50 illustrated in FIG. 2 or the flow redirector 60 illustrated in FIG. 3. Those skilled in the art will recognize that the rotatable ring device 400 is merely schematic and is intended to generically refer to a wide variety of rotatable ring devices. An example of a rotatable ring device that may be adapted for use in the present invention is disclosed in U.S. Pat. No. 4,551,862 to Haber, the entire disclosure of which is hereby incorporated by reference.

Rotatable ring device 400 includes a housing 402 which may be connected to the vessel wall 92 utilizing conventional techniques such as sutures 404. Housing 402 includes one or more rings 406 which are operably connected to a linear actuation cable 408 to cause rotation of the ring or rings 406 substantially as described in Haber '862. The linear actuation cable 408 is connected to a solenoid device 410 which selectively pushes or pulls the linear actuation cable 408 to cause clockwise or counter-clockwise rotation of the rotatable rings 406.

The solenoid device 410 is connected to the control cable 38 which provides a control signal from the control system 40 to activate or deactivate the solenoid device 410 and thereby rotate the rings 406. When activated, the solenoid 410 causes the rotatable rings 406 to constrict the vascular wall 92 and reduce the size of the lumen 94. The internal lumen 94 may be partially or totally occluded by adjusting the degree of rotation of the rings 406. When deactivated, the solenoid device 410 causes the rotatable rings to unconstrict thereby permitting the vascular wall 92 to return to its unconstricted state and restoring the nominal size of the internal lumen 94. The function and use of the rotatable ring device 400 is otherwise substantially the same as the other external compression devices 100, 300 discussed previously.

Refer now to FIG. 10 which shows a side cross-sectional schematic illustration of an external pump 500 in accordance with an embodiment of the present invention. FIG. 10 illustrates the pump 500 in the deactivated state. The external pump 500 may be used for the arterial flow pump 70 illustrated in FIG. 4 or the venous flow pump 80 in FIG. 5.

Those skilled in the art will recognize that the external pump 500 is merely schematic and is intended to generically refer to a wide variety of extraluminal vascular pumps. An example of an extraluminal vascular pump that may be adapted for use in the present invention is disclosed in Dockum et al. '318 mentioned previously.

Extraluminal pump 500 includes a housing 502 which may be connected to the vessel wall 92 utilizing conventional techniques such as sutures 504. Housing 502 includes a plurality of inflatable balloons 506 each having an interior 507 which is in fluid communication with a plurality of fluid lines 508. Fluid communication to each of the balloons 506 is maintained by separate lumens within the fluid line 508 such that the balloons 506 may be inflated independently.

A pressure/vacuum source 110 is fluidly connected to a manifold 510 which sequentially inflates and deflates each of the balloons 506 to cause a sequence of constrictions about the vessel wall 92, thereby creating a pumping action within the vascular lumen 94. The direction and speed of the inflation sequence may be modified to change the pumping direction and flow rate. The pressure/vacuum source 110 is connected to the control cable 38 which provides a control signal from the control system 40 to activate and deactivate the pressure/vacuum source 110 and manifold 510. When activated, the pressure/vacuum source 110 and manifold 510 cause the balloons 506 to sequentially inflate thereby producing the pumping action. After the balloons 506 have been sequentially inflated, the pressure/vacuum source 110 applies a vacuum to deflate the balloons 506. The pressure/vacuum source 110 and manifold 510 may be reactivated to initiate another pumping cycle. If no further pumping action is desired, the pressure/vacuum source 110 maintains a vacuum such that the balloons 506 remain deflated.

If the external pump 500 is used for the arterial flow pump 70 illustrated in FIG. 4, the external pump 500 selectively supplements arterial blood flow and/or perfusion pressure to the renal arteries 200 thereby increasing renal perfusion. If the external pump 500 is utilized for the venous flow pump 80 illustrated in FIG. 5, the external pump 500 reduces blood flow or causes back flow in the renal veins 22 thereby increasing renal back pressure. In either instance, the renovascular perfusion and/or intrarenal pressure are maintained or augmented.

The external pump 500 may utilize hydraulically actuated balloons 506 as illustrated and described, or may utilize hydraulically actuated pistons similar to the embodiment described with reference to FIGS. 8A and 8B. Alternatively, the pistons may be electromagnetically actuated as with a solenoid type device as described in Dockum et al. '318 and as described with reference to the alternative embodiment of FIGS. 8A and 8B. Thus, the external pump 500 may be hydraulically actuated by utilizing balloons 506, or may be hydraulically or electromagnetically actuated by replacing the balloons 506 with pistons slidably disposed in chambers.

Refer now to FIG. 11 which shows a side cross-sectional schematic illustration of an internal pump 600 in accordance with an embodiment of the present invention. FIG. 11 illustrates the intraluminal pump 600 in the static or deactivated state. The intraluminal pump 600 may be utilized for the arterial flow pump 70 illustrated in FIG. 4 or the venous flow pump 80 illustrated in FIG. 5. Those skilled in the art will recognize that the intraluminal pump 600 is merely schematic and is intended to generically wide variety of intraluminal vascular pumps. An example of an intraluminal vascular pump suitable for use in the present invention is disclosed in U.S. Pat. No. 5,692,882 to Bozeman, Jr. et al., the entire disclosure of which is hereby incorporated by reference.

The intraluminal pump 600 includes a housing 602 which may be connected to the vessel wall 92 utilizing the same anchoring techniques used by intravascular stents, grafts and filters. Housing 602 includes proximal and distal struts 603 which support rotatable axle 604. One or more impeller blades 605 are rigidly connected to the axle 604 and rotate relative to the housing 602 and struts 603. When the impeller blades 605 are rotated, blood in the vascular lumen 94 is biased in the proximal or distal direction. Impeller blades 605 may be formed of a ferrous material suitable for forming into permanent magnets. Alternatively, the impeller blades 605 may be formed of a nonferrous material but include a ferrous material disposed thereon for forming into permanent magnets.

The housing 602 includes a plurality of electrical windings 606 which may be selectively activated by electrical cable 608. Electrical cable 608 is connected to power amplifier 610 which may be selectively activated or deactivated by the control system 40 by way of control cable 38. By activating the power amplifier 610, electrical power is supplied to the coil windings 606 in the housing 602. The coil windings 606 generate a magnetic field causing the permanent magnets disposed on the impeller blade 605 to be displaced. Multiple coil windings 606 may be utilized about the periphery of the housing 602 to sequentially activate and deactivate magnetic fields causing rotation of the impeller blades 605. The direction and frequency of the sequential activation may be modified to change the direction and speed of rotation, and thus the direction and degree of pumping action. As an alternative, supplemental fluid may be supplied to the pump 600 by connection to a source of blood within the body or by connection to a fluid reservoir containing a suitable fluid such as saline. The function and use of internal pump 600 is otherwise essentially the same as external pump 500.

Figure 12:
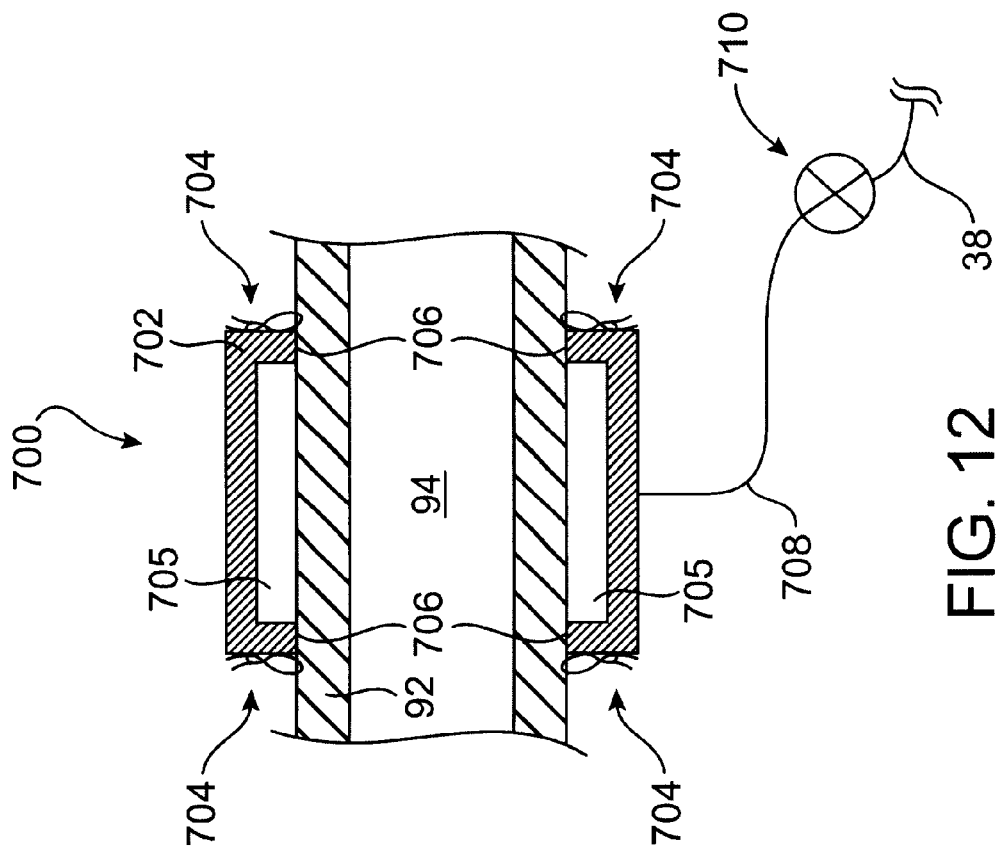
FIG. 12 is a side cross-sectional schematic illustration of an extraluminal site specific drug delivery apparatus.

Refer now to FIG. 12 which shows a side cross-sectional schematic illustration of a drug delivery device 700 in accordance with an embodiment of the present invention. Those skilled in the art will recognize that other site-specific drug delivery devices may be utilized in place of the delivery device 700 illustrated. Delivery device 700 includes a housing 702 which may be connected the vessel wall 92 utilizing conventional techniques such as sutures 705. Housing 702 includes an annular recess 705 which is in fluid communication with a fluid delivery line 708. Annular recess 705 is open to the exterior of the vascular wall 92. Housing 702 includes annular seals 706 disposed proximally and distally of the annular recess 705 to create a fluid tight seal between the housing 702 and the vascular wall 92. By creating a fluid tight seal, the annular seals 706 maintain fluid in the annular recess 705. With this arrangement, fluid delivered to the annular recess 705 via fluid delivery lines 708 remains in intimate contact with the exterior of the vascular wall 92 at the desired location.

Fluid line 708 is connected to a fluid delivery pump/reservoir 710 which is connected to the control cable 38. The control cable 38 provides a control signal from the control system 40 to activate or deactivate the pump/reservoir 710. By selectively activating the pump/reservoir 710, fluid contained in the reservoir 710 is delivered to the annular recess 705 by way of fluid line 708. The fluid contained in the reservoir 710 is preferably a vasoconstrictor such as phenylephrine. Alternatively or in addition, the reservoir may contain a vasodilator such as hydralazine or nitroprusside.

Accordingly, when the pump/reservoir 710 is activated, the vasoconstrictor is delivered to the annular recess 705 thereby constricting the vascular wall 92 and obstructing or reducing the size of the internal lumen 94. Internal lumen 94 may be partially or totally closed by varying the amount and strength of the vasoconstrictor. When deactivated, the pump/ reservoir 710 may deliver a dilution fluid or a vasodilator to reduce or reverse the effects of the vasoconstrictor, thereby permitting or causing the vascular wall 92 to return to its unconstricted state and restoring the nominal size of the internal lumen 94. The function and use of the vasoconstrictor delivery device 700 is otherwise substantially the same as the external compression devices 100, 300 described previously.

From the foregoing, it should be apparent to those skilled in the art that the present invention provides a number of devices 100, 200, 300, 400, 500, 600, 700 and systems 30, 40, 50, 60, 70, 80 and methods by which the real or apparent renovasculature perfusion and intrarenal pressure may be selectively and controllably increased. By selectively and controllably increasing renovascular perfusion and interstitial hydrostatic pressure when the heart is unable to pump sufficient blood or when renal perfusion is suboptimal, the present invention reduces or reverses neurohormonal activation and fluid retention, and thereby minimizes their deleterious effects on the heart, vasculature, kidneys and other body systems.

Those skilled in the art will recognize that the present invention may be manifested in a variety of forms other than the specific embodiments described and contemplated herein. Accordingly, departures in form and detail may be made without departing from the scope and spirit of the present invention as described in the appended claims.

What is claimed is:

1. A method of treating a patient comprising the steps of:
    providing a blood perfusion modification device;
    positioning the blood perfusion modification device in the patient's renovascular circulation or immediately adjacent thereto;
    providing a sensor;
    positioning the sensor in a renal artery or upstream thereof to generate a signal indicative of a need to modify renal perfusion; and
    activating, deactivating or otherwise modifying the blood perfusion modification device as a function of the sensor signal to cause an increase in renal perfusion.

2. A method as in claim 1, wherein the modification device comprises a flow regulator, and wherein the flow regulator is positioned in a renal vein or immediately downstream thereof to create back pressure in the renovascular circulation.

3. A method as in claim 1, wherein the modification device comprises a flow redirector, and wherein the flow redirector is positioned downstream of a renal artery to redirect blood flow to the renal artery.

4. A method as in claim 3, wherein the flow redirector is positioned in a descending aorta downstream of the renal artery to redirect blood flow to the renal artery.

5. A method as in claim 3, wherein the flow redirector is positioned in a common iliac artery downstream of the renal artery to redirect blood flow to the renal artery.

6. A method as in claim 1, wherein the modification device comprises a pump, and wherein the pump is positioned upstream of a renal artery to supplement blood flow therein.

7. A method as in claim 1, wherein the modification device comprises a pump, and wherein the pump is positioned downstream of a renal vein to reduce blood flow or causes back flow therein.

8. A method as in claim 1, wherein the modification device comprises a drug delivery device, and wherein the drug delivery device is positioned patient's renovascular circulation or immediately adjacent thereto.

9. A method as in claim 1, wherein the modification device is positioned intravascularly.

10. A method as in claim 1, wherein the modification device is positioned extravascularly.

11. A method as in claim 1, wherein the sensor generates a signal indicative of pressure, and wherein the modification device is activated, deactivated or otherwise modified when the pressure falls below or rises above a predetermined threshold pressure.

12. A method as in claim 1, wherein the sensor generates a signal indicative of urine production, and wherein the modification device is activated, deactivated or otherwise modified when the urine production falls below or rises above a predetermined threshold value.

13. A method of treating a patient having a clinical condition, the method comprising the steps of:
    diagnosing or monitoring the clinical condition or a sign thereof;
    providing a blood perfusion modification device;
    positioning the blood perfusion modification device in the patient's renovascular circulation or immediately adjacent thereto; and
    activating, deactivating or otherwise modifying the blood perfusion modification device to cause an increase in renal perfusion to thereby treat the clinical condition.

14. A method as in claim 13, further comprising the steps of:
    providing a sensor;
    positioning the sensor in, on or adjacent the patient to generate a signal indicative of a need to modify renal perfusion; and
    wherein the step of activating, deactivating or otherwise modifying the blood perfusion modification device is performed as a function of the sensor signal to cause an increase in renal perfusion to thereby treat the clinical condition.

15. A method as in claim 14, wherein the sensor is positioned upstream of the modification device.

16. A method as in claim 13, wherein the clinical condition comprises congestive heart failure, and wherein the diagnosing or monitoring step comprises diagnosing or monitoring the congestive heart failure condition.

17. A method as in claim 13, wherein the clinical condition comprises hypertension, and wherein the diagnosing or monitoring step comprises diagnosing or monitoring the hypertension condition.

18. A method as in claim 13, wherein the clinical condition comprises renal failure, and wherein the diagnosing or monitoring step comprises diagnosing or monitoring the renal failure.

19. A method as in claim 13, wherein the clinical condition comprises a cardiovascular or renal abnormality, and wherein the diagnosing or monitoring step comprises diagnosing or monitoring the cardiovascular or renal abnormality.

20. A method of treating a patient comprising the steps of:
    providing a blood perfusion modification device;
    positioning the blood perfusion modification device in the patient's renovascular circulation or immediately adjacent thereto;
    providing a sensor;

positioning the sensor in a renal artery or upstream thereof to generate a signal indicative of a need to modify renal perfusion; and activating, deactivating or otherwise modifying the blood perfusion modification device as a function of the sensor signal to cause an increase in renal perfusion, wherein the sensor generates a signal indicative of urine production, and wherein the modification device is activated, deactivated or otherwise modified when the urine production falls below or rises above a predetermined threshold value.

21. A method as in claim 20, wherein the sensor is positioned upstream of the modification device.

22. A method as in claim 20, wherein the modification device comprises a flow regulator, and wherein the flow regulator is positioned in a renal vein or immediately downstream thereof to create back pressure in the renovascular circulation.

23. A method as in claim 20, wherein the modification device comprises a flow redirector, and wherein the flow redirector is positioned downstream of a renal artery to redirect blood flow to the renal artery.

24. A method as in claim 23, wherein the flow redirector is positioned in a descending aorta downstream of the renal artery to redirect blood flow to the renal artery.

25. A method as in claim 23, wherein the flow redirector is positioned in a common iliac artery downstream of the renal artery to redirect blood flow to the renal artery.

26. A method as in claim 23, wherein the modification device comprises a pump, and wherein the pump is positioned upstream of a renal artery to supplement blood flow therein.

27. A method as in claim 20, wherein the modification device comprises a pump, and wherein the pump is positioned downstream of a renal vein to reduce blood flow or causes back flow therein.

28. A method as in claim 20, wherein the modification device comprises a drug delivery device, and wherein the drug delivery device is positioned patient's renovascular circulation or immediately adjacent thereto.

29. A method as in claim 20, wherein the modification device is positioned intravascularly.

30. A method as in claim 20, wherein the modification device is positioned extravascularly.

* * * * *

UNITED STATES PATENT AND TRADEMARK OFFICE
CERTIFICATE OF CORRECTION

| | | |
|---|---|---|
| PATENT NO. | : 6,616,624 B1 | Page 1 of 1 |
| APPLICATION NO. | : 09/702089 | |
| DATED | : September 9, 2003 | |
| INVENTOR(S) | : Robert S. Kieval | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 247 days.

Signed and Sealed this

Thirteenth Day of March, 2012

David J. Kappos
*Director of the United States Patent and Trademark Office*